United States Patent [19]

Morgan

[11] Patent Number: 4,930,500

[45] Date of Patent: Jun. 5, 1990

[54] SELF-ADHESIVE BANDAGE

[76] Inventor: Burton D. Morgan, 1790 Stoney Hill Dr., Hudson, Ohio 44236

[21] Appl. No.: 217,422

[22] Filed: Jul. 11, 1988

[51] Int. Cl.$^5$ .............................................. H61L 15/00
[52] U.S. Cl. ...................................... 128/156; 128/155
[58] Field of Search ................................. 128/155, 156

[56] References Cited

U.S. PATENT DOCUMENTS 4,587,284  5/1986  Lüissi et al. ....................... 524/35 X
4,631,227  12/1986  Nakamura ........................ 128/156 X Primary Examiner—Randall L. Green
Assistant Examiner—N. Paul
Attorney, Agent, or Firm—Oldham & Oldham Co.

[57] ABSTRACT

A self adhesive bandage which comprises a hydrophilic gel located on a bandage carrier strip at the point of the strip to be positioned against a wound. Portions of the same surface of the carrier strip are also coated with a pressure sensitive adhesive, allowing the bandage to be secured to the skin. The gel-side surface is covered with a strip of removable release paper until the bandage is to be used, in order to preserve its sterility. The gel comprises water and a polyol mixed with the reaction product of a bis crosslinking agent with an acrylamide compound.

6 Claims, 1 Drawing Sheet

SELF-ADHESIVE BANDAGE

TECHNICAL FIELD

This invention relates to improved self-adhesive wound dressings, and bandages. More particularly, this invention relates to self-adhesive bandages which are hydrophilic in character, and which consequently, exhibit little or no tendency to adhere to a wound on which they have been placed. Specifically, this invention relates to self-adhesive bandages which are covered with an air-permeable, hydrophilic, gel-type material over the portion of the bandage to be disposed adjacent to the wound to be protected thereby, thus making removal of the bandage both easy and painless.

BACKGROUND OF THE INVENTION

In protecting minor cuts, scratches, abrasions, and similar injuries, particularly on a temporary, self-treatment basis, the use of the so-called self-adhesive bandage has become widespread. Bandages of the self-adhesive type basically involve a length of adhesive tape with a pad of gauze, or similar material, located in the center portion thereof, the whole being covered by a separable layer of "release" paper which preserves the sterility of the gauze, and renders the adhesive properties of the tape inoperative until the paper is removed prior to application of the bandage. Such bandages come in a variety of shapes and sizes and are both inexpensive and easy to apply, which helps to account for their widespread popularity.

One drawback exhibited by such bandages, however, stems from the fact that the gauze portion of the bandage tends to become saturated with the natural exudate from the wound, and as the latter dries, it tends to form an adherent bond between the bandage and the wound. When an attempt is subsequently made to remove the bandage, the result is not only painful, but the wound protecting incrustation, or scab, is often torn from the wound, making the wound vulnerable to infection.

In an attempt to avoid the problem, it has been proposed to reduce the affinity of the gauze for the wound fluids, for example, by forming the gauze from hydrophobic, non-wetting, fibers, particularly synthetic fibers. Unfortunately, such attempts have not totally resulted in avoiding unwanted adherency, due to the tendency of the wound fluids to penetrate around the fibres, into the interior of the gauze. There, the fluids tend to solidify, creating the objectionable bond referred to. It has also been proposed to substitute sheets of hydrophobic materials, rather than gauze adjacent to the wound surface to avoid formation of the adhesive bonds. However, due at least in part to surface irregularities, which also tend to facilitate formation of the bonds referred to, the use of such materials has not been totally successful.

DISCLOSURE OF THE INVENTION

In light of the foregoing, therefore, it is a first aspect of this invention to provide a bandage of the self-adhesive type that exhibits little or no tendency to form an adhering bond with the wound on which it is placed.

A second object of the invention is to furnish a self-adhesive bandage that avoids bonding with the wound over which it is placed through provision of a hydrophilic wound contacting surface.

A further aspect of the invention is to provide a self-adhesive bandage that employs a gel-time material on its wound-contacting surface, as opposed to gauze or other material.

An additional aspect of the invention is to make available a self-adhesive bandage which provides an air-permeable, gel-like medium adjacent to the wound surface, thus promoting healing.

Another aspect of the invention is to provide a bandage which may be easily applied by unskilled individuals, and one that is readily removed without causing pain or injury to the wound.

The preceding and other aspects of the invention are provided by a self-adhesive bandage comprising in combination:

a carrier strip;

an air-permeable, hydrophilic gel material, and a removable release paper wherein said carrier strip is formed from a fabric, and wherein the surface of said carrier strip that is intended for placement against a wearer's skin includes a first portion thereof coated with a pressure sensitive adhesive, and a second portion thereof coated with said gel material, and wherein further, said release paper is held over said surface by said pressure-sensitive adhesive.

BRIEF DESCRIPTION OF THE DRAWINGS

The invention will be better understood when reference is had to the following drawings, and in which like numbers refer to like parts, and in which.

DETAILED DESCRIPTION OF THE INVENTION

Figure 1:
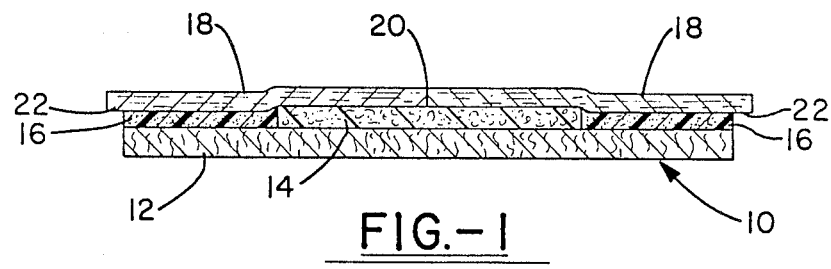
FIG. 1 is a sectional view of a self-adhering bandage of the invention along line 1—1 of FIG. 2.
Figure 2:
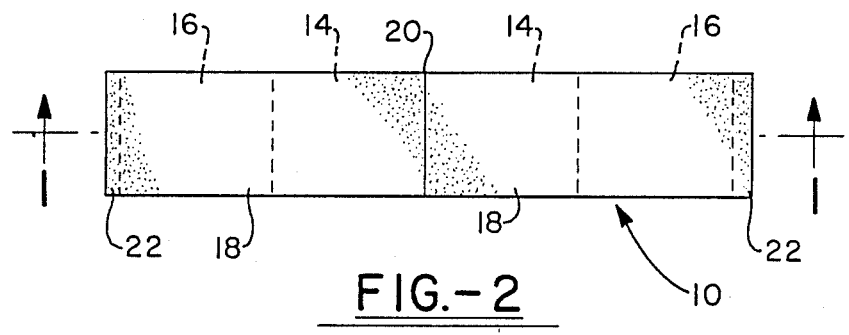
FIG. 2 is a top plan view of a self-adhering bandage of the invention.

FIG. 1 is a sectional view of a self-adhering bandage, generally 10, along line 1—1 of FIG. 2. The Figure shows a layer of the gel material 14 disposed on carrier strip 12, between layers of pressure sensitive adhesive 16, also disposed thereon. Covering the gel material 14 is a release paper 18, held in place by its adhering contact with the pressure sensitive adhesive 16. The release paper 18 is scored in the center at 20 in order to facilitate its removal. Lift tabs 22 extend beyond the ends of the bandage laminate comprising the carrier strip 12, together with the pressure sensitive adhesive 16 and the gel material 14, allowing the paper to be grasped and readily removed from the laminate.

The term "gel material" as referred to in connection with the layer 14, is meant to describe the relatively thin, semi-liquid, jelly-like material, which may vary considerably in consistency as hereinafter described, that is hydrophilic in nature, and which preferably exhibits hygroscopic tendencies. The gel material is basically a mixture of an acrylamide compound, a bis-functional cross-linking agent, a polyol and water. The texture of the material, as well as its "consistency" depends upon the degree of cross-linking, as well as the amount of polyol and water employed. The function of the gel is to provide a moisturized interface between the bandage carrier strip 12 and the wound, thus avoiding any tendency of the incrustations produced in the process of healing from adhering to the carrier strip.

While a variety of fabric materials may be used for the carrier strip 12, the use of a non-woven fabric is particularly suitable for purposes of the invention, since among other advantages, it provides interstices between the filaments making up the fabric of a type which assure adequate adhesion between the gel material 14 and the carrier strip 12. Non-woven cottons are particularly useful as carrier strips, although polyesters, or other materials may also be used.

The release paper may be any of the types widely known in the art, which exhibit little or no tendency to adhere to adhesive materials with which they are in contact, usually due to protective coatings on the paper. Any of various weights of paper may be used, for example, 60 pound per ream, and different kinds of paper may be employed such as white sulphite paper, white coated kraft paper, or others.

The pressure sensitive adhesives suitable for purposes of the invention are also well-known in the art, those of the acrylic type, or elastomers mixed with resins, being typical.

The bandage construction will depend upon the size of the wound to be treated, the nature of the materials from which the bandage is made, and similar considerations; however ordinarily, the carrier strip 12 will be from about 2 to 5 mils in thickness, while the gel material will be about 1 to 2 mils thick, and the pressure sensitive adhesive about 1 to 3 mils in thickness.

The bandage is applied by removing the release paper 22, avoiding contact of the surface of the gel material 14 in the process, and thereafter applying the bandage so that the gel material is located against the wound to be protected. The pressure sensitive adhesive portions 16 are then pressed firmly against the skin surrounding the wound, firmly securing the bandage to the skin around the wound. Once applied, the gas-permeation characteristics of the gel material allow air to penetrate to the surface of the wound, promoting the healing process. Besides protecting the gel material from any tendency to dry out, due to its hydrophilic and hygroscopic nature, the polyol present has an antiseptic quality, tending to supress infection during the healing process which might otherwise be caused by septic material either present in the wound initially, or that entering the wound despite the protective barrier of the carrier strip.

FIG. 2 shows a top plan view of the self-adhering bandage 10 of the invention illustrating further details of the portion of the bandage on which the gel material 14 is disposed, as well as the bandage portions covered by the pressure sensitive adhesive 16.

As previously described, the gel material contains a cross-linked reaction mixture of a monomer with a cross-linking agent, as well as a polyol type material, and water. The monomer, which ordinarily will constitute about 10 to 30% by weight of the gel system, will be a compound having the general formula

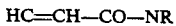

where R may be hydrogen or a hydrocarbon radical, preferably a methyl radical, although it may be a radical containing up to 6, or even more carbon atoms. Acrylamide is the preferred monomer for the purposes of the invention.

The cross-linking agent will be of the bis-functional type, and may include such compounds as N, N'methylene bis acrylamide, N-N'(1,2 dihydroxy methylene)-bis acrylamide, bis-acrylylcystamine, and others. Such cross-linking agents have the ability to provide a cross-linked material that is sufficiently gas permeable in the presence of water to allow air to pass relatively freely therethrough. While various amounts of cross-linking compounds may be employed, an amount in the range of from about 0.02% to 0.6% on a weight basis, based upon the amount of monomer in the system, will usually be employed. Use of a lesser amount of cross-linking agent runs the risk of producing an excessively viscous gel, while much more than that amount has a tendency to result in a relatively stiff gel.

Ordinarily from about 0.5% to 5.0% by weight, based on the weight of the total gel system, of a polyol will be added, particularly to promote water retention by the system. Suitable polyols include materials such as glycols, including particularly glycerol, sugars such as sucrose, fructose, or the like, and others.

In preparing the gel, the components described are combined with water, which may make up from about 50% to 90% of the gel system, and a catalyst is added to initiate the reaction. The order of addition of components may be altered if desired. The catalyst system is of the free radical type including, for example, an ammonium peroxy disulfate free-electron donator, and a tetraethylene methylenediamine catalyst, as well as similar systems known in the art. While such catalyst systems, which may be used in varying amounts, i.e., from about 0.1% to 0.3%, or greater, are capable of initiating the reaction at ambient room temperatures, the reaction rate can be accelerated by elevated temperatures, or through the use of the more concentrated catalyst systems. The reaction time provided will depend upon such factors.

In fabricating the bandage, the pressure sensitive adhesive is applied to each end of the carrier strip by any of the well-known methods, while the gel material can be disposed on the center portion of the carrier strip in a variety of ways. For example, the gel reaction mixture can be applied to the carrier strip while the cross-linking reaction is still in process, providing an "in-situ" gel formation, the reactants partially penetrating the carrier strip before the gel is completely formed, thereby firmly locking it in place. Alternatively, the nature of the gel, i.e., its viscosity and natural tendency to adhere to a substrate, may allow its placement at the desired location on the carrier strip after the gel has been formed. In the latter case, the necessary adherency between the carrier strip is either already sufficient as a result of the natural tackiness of the gel, or it can be made so by a brief heating of the bandage. Thereafter, the protective release paper is applied to complete the bandage.

Self-adhesive bandages of the type described may be made in a variety of sizes and shapes, for example, rectangular, square, round, or otherwise. However, rectangular self-adhesive bandages of approximately three inches long by seven inches wide are typical.

The bandages may be prepared individually, or they may more conveniently be manufactured in strips of adjacent bandages; the latter can then be severed to form individual bandages. The bandage strips may also be packaged in the form of rolls in dispenser boxes which allow bandages to be withdrawn in the form of a continuous "tape" and removed from the release paper to which they are attached as single bandages.

While in accordance with the patent statutes, the preferred embodiment and best mode has been presented, the scope of the invention is not limited thereto, but rather is measured by the scope of the attached claims.

What is claimed is:

1. A self-adhesive bandage comprising in combination:
   a carrier strip;
   an air-permeable, hydrophilic gel material further comprising the reaction product of an acrylamide compound, and a bis-functional cross-linking agent, mixed with water and a hydrophilic polyol; and
   a removeable release paper, wherein said carrier strip is formed from a fabric, and wherein the surface of said carrier strip that is intended for placement against a wearer's skin includes a first portion thereof coated with a pressure sensitive adhesive, and a second portion thereof coated with said gel material, and
   wherein further, said release paper is held over said surface by said pressure sensitive adhesive.

2. A bandage according to claim 1 wherein said acrylamide compound is selected from the group consisting of acrylamide, and substituted derivatives thereof, and wherein said cross-linking agent is a bis-acrylamide, and wherein further, said polyol is selected from the group consisting of sugars, glycerol, and glycol.

3. A bandage according to claim 1 wherein said fabric is a non-woven fabric.

4. A bandage according to claim 2 wherein said polyol comprises a sugar.

5. A bandage according to claim 2 wherein said polyol comprises glycerol.

6. A bandage according to claim 2 wherein said polyol comprises glycol.

* * * * *